US012108809B1

(12) United States Patent
Senter et al.

(10) Patent No.: US 12,108,809 B1
(45) Date of Patent: *Oct. 8, 2024

(54) AEROSOL PRESSURIZED DELIVERY DEVICE AND METHODS FOR MANUFACTURE AND USE OF THE SAME

(71) Applicant: Air 2 LLC, Centennial, CO (US)

(72) Inventors: Robert L. Senter, Centennial, CO (US); Robert E. Matuszewski, Centennial, CO (US)

(73) Assignee: Air 2, LLC, Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/639,546

(22) Filed: Apr. 18, 2024

Related U.S. Application Data

(63) Continuation-in-part of application No. 18/197,686, filed on May 15, 2023, which is a continuation-in-part of application No. 18/300,992, filed on Apr. 14, 2023, now Pat. No. 12,016,401.

(60) Provisional application No. 63/331,497, filed on Apr. 15, 2022.

(51) Int. Cl.
*A24F 42/20* (2020.01)
*A24B 15/167* (2020.01)
*A24F 42/60* (2020.01)

(52) U.S. Cl.
CPC ............ *A24F 42/60* (2020.01); *A24B 15/167* (2016.11); *A24F 42/20* (2020.01)

(58) Field of Classification Search
None
See application file for complete search history.

(56) References Cited

U.S. PATENT DOCUMENTS

| | | | |
|---|---|---|---|
| 8,256,433 B2 | 9/2012 | Gonda | |
| 9,096,371 B2 | 8/2015 | Allsop | |
| 10,683,159 B2 | 6/2020 | Har-Shai | |
| 12,016,401 B2 * | 6/2024 | Senter et al. | A61M 15/009 |
| 2006/0211589 A1 | 9/2006 | Godfrey et al. | |
| 2007/0051363 A1 | 3/2007 | Andrus et al. | |
| 2008/0138423 A1 | 6/2008 | Gonda | |
| 2009/0065533 A1 | 3/2009 | Warby et al. | |
| 2012/0171259 A1 | 7/2012 | Qazi et al. | |
| 2016/0121059 A1 | 5/2016 | Child et al. | |
| 2017/0252300 A1 | 9/2017 | Modi | |

(Continued)

FOREIGN PATENT DOCUMENTS

| | | |
|---|---|---|
| GB | 2544477 A | 5/2017 |
| WO | 2023002194 A1 | 1/2023 |

OTHER PUBLICATIONS

International Search Report from related PCT Application No. PCT/US2024/029212. 3 Pages. Jul. 3, 2024.

(Continued)

*Primary Examiner* — Dionne W. Mayes
(74) *Attorney, Agent, or Firm* — FisherBroyles LLP; Ian R. Walsworth

(57) ABSTRACT

The present invention improves and enhances the delivery of one of an aerosolized micellized formula by use of an aerosol pressurized inhalation delivery device. The device may include one or more replaceable or reusable components, including but not limited to a canister and an actuator. Methods for using the device to deliver a continuous dosage via the delivery device are also described herein.

11 Claims, 11 Drawing Sheets

(56) References Cited

U.S. PATENT DOCUMENTS

2020/0156826 A1 5/2020 Kilduff et al.
2023/0080276 A1 3/2023 Zambelli

OTHER PUBLICATIONS

Written Opinion of the ISA from related PCT Application No. PCT/US2024/029212. 10 Pages. Jul. 3, 2024.

* cited by examiner

FIG. 14
FIG. 15
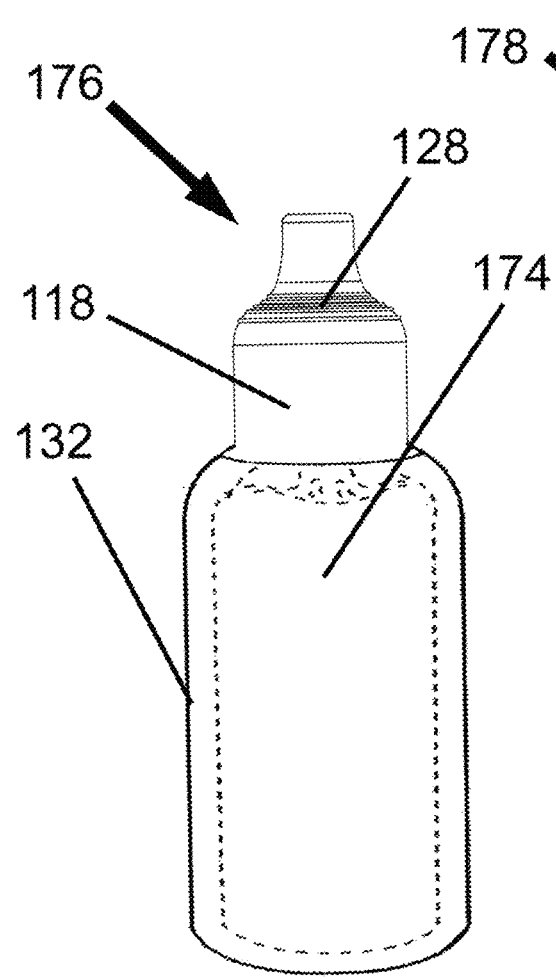
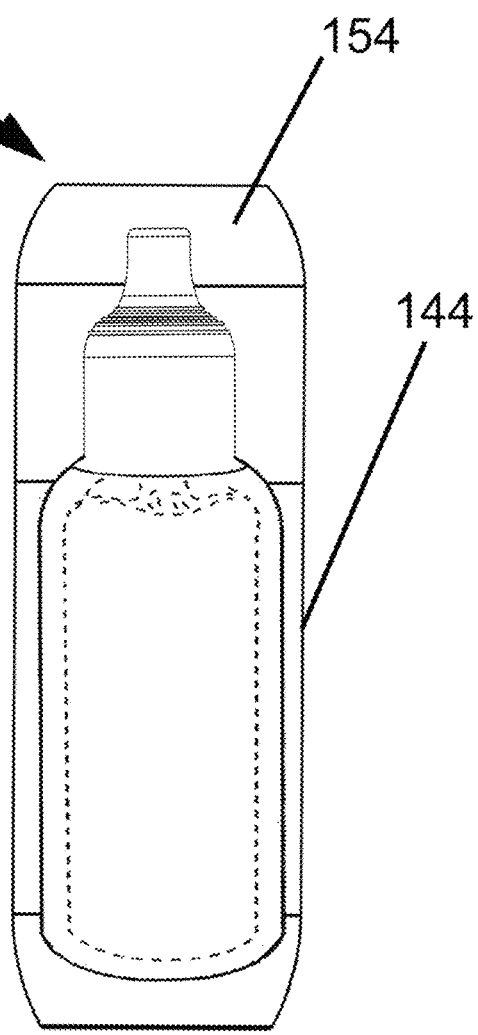

AEROSOL PRESSURIZED DELIVERY DEVICE AND METHODS FOR MANUFACTURE AND USE OF THE SAME

CROSS REFERENCE TO RELATED APPLICATIONS

The present application is a continuation-in-part of co-pending U.S. patent application Ser. No. 18/197,686, filed May 15, 2023, which is a continuation-in-part of U.S. patent application Ser. No. 18/300,992, filed on Apr. 14, 2023, which in turn claims priority under 35 U.S.C. § 119 (e) to U.S. Provisional Patent Application Ser. No. 63/331,497, filed Apr. 15, 2022, the entireties of which are incorporated herein by reference.

FIELD OF THE INVENTION

Aspects of the present disclosure relate generally to the field of medical devices, and more particularly to a device for delivering and related systems and methods, and more particularly an aerosol pressurized inhalation delivery device that eliminates a cartridge or reservoir or pod, the heating element and power source or battery and secondhand smoke.

BACKGROUND

The Center for Disease Control and Prevention ("CDC") validates that smoking can cause cancer, most often lung cancer, and then block the human body from fighting the disease. It is well known in the art that the poisons in cigarette smoke can affectively weaken the body's immune system, creating a greater challenge to kill cancer cells which grow and multiply over time. More specifically, the poisons in tobacco smoke can damage or change a cell's DNA and once damaged, those cells can begin growing out of control and create a cancer tumor. In addition, vaping has become increasingly popular in recent years among teenagers and young adult populations, and the known additive nature of nicotine among youth and young adults has developed into a major health concern. These and related issues have become a considerable health risk, including for people who do not smoke or vape but are exposed to the secondhand smoke of another. Cigarette smoking remains the leading cause of preventable disease, disability, and death in the United States, accounting for more than 480,000 deaths every year, or about 1 in 5 deaths. In 2021, nearly 12 of every 100 U.S. adults aged 18 years or older (11.5%) currently smoked cigarettes. This means an estimated 28.3 million adults in the United States currently smoke cigarettes. More than 16 million Americans live with a smoking-related disease. Secondhand smoke exposure resulted in more than 42,000 deaths: more than 41,000 adults and nearly 900 infants. Blacks accounted for 13% of all deaths but 24% to 36% of infant deaths. Secondhand smoke attributable deaths resulted in a loss of nearly 600,000 years of potential life lost and $6.6 billion of lost productivity, or $158 000 per death. The value of lost productivity per death was highest among Blacks ($238 000) and Hispanics ($193 000).

Vaping is a process of aerosolizing a solution and inhaling it into the lungs using an electronic cigarette (e-cigarettes) or other vaping device that serves as an alternative to conventional smoking. During the vaping process, e-cigarettes heat a liquid into an aerosol that the user inhales into their lungs, and commonly comprise a replaceable cartridge. A typical e-cigarette cartridge (also referred to as a reservoir or pod) contains four basic ingredients: water; nicotine; flavorings; and, a propylene or vegetable glycerin base commonly referred to as e-liquid. Consumers may choose from a wide variety of vapes and e-cigarette products that contain nicotine, flavorings, and other additives.

There are a variety of devices known in the art of vaping. For example, e-cigarettes or "e-cigs," "cigalikes," "e-hookahs," "mods," "vape pens," "vapes," and "tank systems" are vaping devices existing in the art today. By way of example, U.S. Pat. No. 8,511,318 describes an e-cigarette device that is comprised of a cylindrical shell containing an e-cigarette cell, a nicotine solution, a control circuit, and an electro-thermal vaporization nozzle. The device allows a person to suck air through an air suction fitting on one end of the shell, which the patent describes as beneficial as it eliminates tar from the nicotine solution and reduces the risk of fire between inhalations. Another example is provided in U.S. Pat. No. 9,737,093, which describes an e-cigarette device having a separate cartridge and vaporizer unit. The separate cartridge unit comprises a liquid with a seal that keeps the liquid safely within the cartridge tube, but may be pierced by a piercer prior to use. The piercer is described as part of the vaporizer unit, which further comprises a heater and an electronic circuit electrically connected to a battery. Notably, the prior art does not disclose a device for providing an aerosolized and/or micellized liquid nicotine formula. The prior art also fails to disclose an actuator that provides a continuous dosage such that a variable amount of the micellized liquid nicotine formula may be inhaled by depressing and holding down the actuator. There are other problems with the prior art, including malfunctions with the electronic circuitry, battery failure, mechanical failure, leaking and/or harmful exposure to the liquid or other substance contained by the cartridge, and other problems addressed by the present disclosure.

Although numerous other prior art solutions have attempted to improve upon vaping and e-cigarette devices, none of the solutions effectively provides a safer aerosolized delivery device that can provide a continuous amount of micellized liquid nicotine formula that decreases the amount of nicotine inhaled by up to 80%. A number of other challenges and deficiencies in the art still persist or remain completely unsolved. It is with respect to these and other problems that the present disclosure is contemplated, as will be described in greater detail below.

SUMMARY

Aspects of the present disclosure relate to an aerosol pressurized inhalation delivery device having an actuator, continuous valve, receptacle housing and metal canister allowing a micellized liquid nicotine formula to be expelled through the actuator discharge nozzle and inhaled directly into the lungs by the user. Depressing and holding down the actuator delivers a continuous amount of micellized liquid nicotine formula passing from the continuous valve through the actuator discharge nozzle. It is up to the user to determine the amount of micellized liquid nicotine formula to be inhaled that will satisfy the desire for nicotine. The continuous valve allows the user to inhale a small amount of micellized liquid nicotine formula considered to be less than 100 microliters or greater than 100 microliters. The aerosol pressurized inhalation delivery device eliminates the use of cartridges or reservoirs or pods, the heating element and power source or battery, secondhand smoke and delivers up to an 80% decrease of nicotine while delivering an equivalent feeling of pleasure to the user. According to a first aspect of the present disclosure, the invention relates to a sublingual delivery system, comprising: a housing comprising: a base portion comprising a recessed lip; a cap portion dimensioned to receive the recessed lip of the base portion such that the base portion and cap portion are connected and aligned along a common axis; and the base portion and cap portion both comprise an internal void; and a pressurized sublingual delivery device comprising: a mouthpiece integral with an actuator; an actuator discharge nozzle; a metered valve; a metal canister; and a cylindrical receptacle housing; wherein the metal canister contains a micellized liquid formula and a propellant; wherein the metered valve is crimped to the metal canister wherein the actuator is in contact with and supported by a surface of the metered valve, and is movably coupled to the cylindrical receptacle housing; wherein the metal canister is positioned within the cylindrical receptacle housing; wherein the mouthpiece, metal canister, metered valve, actuator and cylindrical receptacle housing are all in alignment about the common axis; wherein the pressurized sublingual delivery device is positioned within the internal void; and wherein the actuator and the metered valve are configured such that upon axial movement of the actuator with respect to the metered valve, in the direction of the cylindrical receptacle housing, a predetermined dosage of micellized liquid formula is supplied from the metal canister. According to another aspect of the present disclosure, the invention relates to an aerosol pressurized inhalation delivery device having an actuator, continuous valve, receptacle housing, and metal canister containing a micellized liquid nicotine formula and propellant such as Zephex® 152a that when combined makes the micellized liquid nicotine formula and propellant homogeneous, allowing the micellized liquid nicotine formula to be expelled as an aerosol and inhaled into the lungs with the depression of the actuator.

According to another aspect of the present disclosure, the device comprises a metal canister pressurized with a propellant, such as Zephex® 152a, and may further comprise a crimped continuous valve attached to the canister. In use, the canister may be inserted into a receptacle housing, and the actuator may further comprise a child resistant protective cap to be placed over the actuator.

According to one specific aspect, the present disclosure relates to an aerosol pressurized inhalation delivery device comprising: a continuous valve crimped to a metal canister; an actuator positioned over a continuous valve; a micellized liquid nicotine formula residing within the metal canister; a liquid propellant residing within the metal canister; a metal canister residing within a receptacle housing; and a child resistant cap place over the receptacle housing.

According to yet another specific aspect, the present disclosure relates to a method of delivering a micellized liquid formula comprising coupling a continuous valve on a metal canister containing micellized liquid formula; placing the metal canister and continuous valve into a receptacle housing; positioning an actuator above the continuous valve; activating the actuator by depressing the actuator downward against the continuous valve; piercing a diaphragm on the metal canister with a valve stem associated with the continuous valve; delivering, under pressure, a volume of micellized liquid formula from the metal canister, through the continuous valve and discharge nozzle.

According to one aspect, the invention comprises a non-combustible, smoke-free device for delivering an aerosolized nicotine (which according to one embodiment is 99.9% pure tobacco). In embodiments, the device has no heat, no battery, no oil, no secondhand smoke and greatly reduces the risk of harm during use of the device. The device preferably comprises a proprietary water-soluble homogeneous micellized liquid nicotine formula that reduces the nicotine content by up to 80% compared to electronic nicotine delivery systems ("ENDS").

According to embodiments, the device may be manufactured utilizing a process or processes consistent with, or otherwise in observation of, Environmental Protection Agency and U.S. Food & Drug Administration regulatory guidelines. In embodiments, all ingredients of the micellized liquid nicotine formula are FDA and GRAS compliant, by the Natural & Non-Prescription Product Group. In embodiments, the invention is manufactured utilizing pharmaceutical grade equipment and components.

The devices and components described herein may comprise one or more of a polymeric material and a metallic material. More particularly, the present disclosure may be constructed of materials known to provide, or predictably manufactured to provide the various aspects of the present disclosure. These materials may include, for example, carbon fiber, ABS plastic, polyurethane, polyethylene, photopolymers, resins, fiber-encased resinous materials, rubber, latex, synthetic rubber, synthetic materials, polymers, and natural materials. These materials may further include, for example, stainless steel, titanium alloy, metal alloy, chromium alloy, and other metals or metal alloys.

In one embodiment, at least a portion of the delivery device described herein is reusable. Optionally, a portion of the delivery device is disposable, but in other embodiments the entire delivery device may be reusable or disposable after a set number of uses.

One having skill in the art will appreciate that embodiments of the present disclosure may have various sizes. The sizes of the various devices or their components may be sized based on various factors including, for example, the anatomy of the user, such as the height and weight of the person operating the device, or other physical features of replaceable or reusable components used with the devices described herein, including, for example, width, length and thickness, and the intended dosage(s) provided by the device.

These and other features, utilities, and advantages of the various embodiments of the present invention will be apparent from the following more particular descriptions of the embodiments of the invention as illustrated in the accompanying drawings and defined in the appended claims.

Certain terms are used throughout the following description and claims to refer to a particular system or device components. As one skilled in the art will appreciate, companies may refer to a component by different names. This document does not intend to distinguish between components that differ in name but not function.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

Unless otherwise indicated, all numbers expressing quantities, dimensions, conditions, and so forth used in the specification and claims are to be understood as being approximations which may be modified in all instances as required for a particular application of the novel apparatus described herein.

In the following disclosure, the use of "including," "comprising," or "having" and variations thereof herein is meant to encompass the items listed thereafter and equivalents thereof as well as additional items. Accordingly, the terms "including," "comprising," or "having" and variations thereof can be used interchangeably herein. In the claims, the terms "including" and "comprising" are used in an open-ended fashion, and thus should be interpreted to mean "including, but not limited to".

The term "a" or "an" entity, as used herein, refers to one or more of that entity. As such, the terms "a" (or "an"), "one or more" and "at least one" can be used interchangeably herein.

The term "determine" and variations thereof, as used herein, are used interchangeably and include any type of methodology, process, mathematical operation, or technique.

The term "couple" or "couples" is intended to mean either an indirect or direct connection. When used in a mechanical context, if a first component couples or is coupled to a second component, the connection between the components may be through a direct engagement of the two components, or through an indirect connection that is accomplished via other intermediate components, devices and/or connections. In addition, when used in an electrical context, if a first device couples to a second device, that connection may be through a direct electrical connection, or through an indirect electrical connection via other devices and connections. Connections can occur in a unidirectional, bidirectional or variable directional manner over all known means of network connectivity.

By way of providing additional background, context, and to further satisfy the written description requirement, the following are incorporated by reference in their entireties for the express purpose of explaining and further describing the various devices and apparatus that may be associated with aerosol and micellized nicotine delivery, in general: U.S. Pat. Nos. 8,511,318, 9,737,093, and 11,172,704.

The Summary is neither intended nor should it be construed as being representative of the full extent and scope of the present disclosure. The present disclosure is set forth in various levels of detail in the Summary as well as in the attached drawings and the Detailed Description and no limitation as to the scope of the present disclosure is intended by either the inclusion or non-inclusion of elements, components, etc. in this Summary. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below.

BRIEF DESCRIPTION OF THE DRAWINGS

Many aspects of the disclosure can be better understood with reference to the following drawings. While several implementations are described in connection with these drawings, the disclosure is not limited to the implementations disclosed herein. On the contrary, the intent is to cover all alternatives, modifications, and equivalents.

In certain instances, details that are not necessary for an understanding of the disclosure or that render other details difficult to perceive may have been omitted. It should be understood, of course, that the disclosure is not necessarily limited to the particular embodiments illustrated in the following Figures. In the drawings:

FIG. 14 is another side view depicting the bag-on-valve propellant system of FIG. 13, wherein the bag-on-valve bag is substantially filled with micellized liquid nicotine formula;

FIG. 15 is a side and cross-sectional view of the bag-on-valve system of FIG. 14 inserted into a receptacle housing with a child-resistant cap securely attached.

Figure 1:
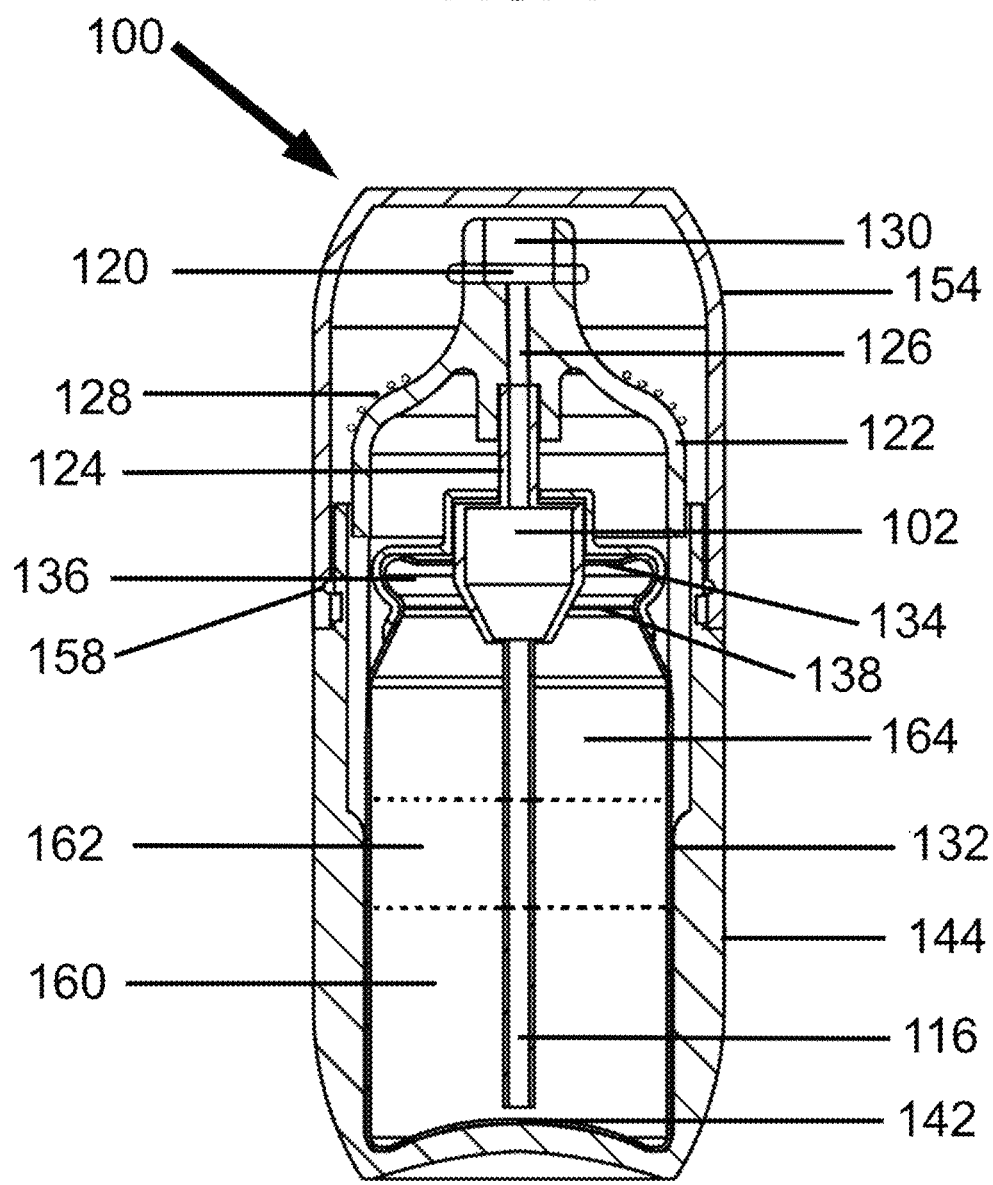
FIG. 1 is a cross-sectional view of a first embodiment of the aerosol inhalation pressurized delivery device according to a preferred embodiment depicting an actuator, continuous valve, receptacle housing and metal canister.

It should be understood that the drawings are not meant to be and/or are not necessarily to scale. In addition, certain elements are identified by a reference number to illustrate a specific feature of the embodiment, while in other drawings those specific features are not identified.

In certain embodiments, the invention may comprise fewer than all components depicted in any of the appended drawing figures. In this regard, the drawing figures are intended as exemplary embodiments only, and components are described in connection with these exemplary embodiments for the purpose of streamlining the disclosure.

For ease of reference, the following is a listing of components depicted in the drawing figures, some of which are described in greater detail herein:

100 aerosol pressurized inhalation delivery device
102 continuous valve
104 valve stem
106 valve internal gasket
108 valve external gasket
110 valve mounting cup
112 valve spring
114 valve continuous flow chamber 116 valve dip tube
118 actuator
120 actuator discharge nozzle
122 actuator base receptor
124 actuator valve sleeve
126 actuator discharge channel
128 actuator ridged finger control
130 actuator discharge area
132 metal canister
134 metal canister lip
160 metal canister throat
162 metal canister rim
140 metal canister base
142 metal canister concave base bottom
144 protective plastic canister receptacle housing
146 plastic base receptacle rim
148 plastic base receptacle child resistant cap channels
150 plastic base receptacle recessed lip
152 protective plastic canister base
154 protective plastic canister receptacle child resistant cap
156 protective plastic canister receptacle child resistant cap base
158 plastic child resistant ribs
160 liquid propellant
162 liquid micellized nicotine formula
164 air pocket
166 bag-on-valve system
168 bag-on-valve continuous valve
170 bag-on-valve
172 compressed air propellant
174 bag-on-valve inflated bag
176 aerosol pressurized inhalation delivery device having a bag-on valve system

DETAILED DESCRIPTION

The following disclosure is directed to various embodiments, including those depicted in FIGS. 1-15 appended hereto. Embodiments described herein relate to an aerosol pressurized inhalation delivery device (and methods for fabricating and using the same) that delivers a a desired dose of micellized liquid nicotine formula with the depression of the actuator. The actuator is secured to the continuous valve which is crimped to a metal canister. The metal canister is positioned inside the receptacle housing which can be Fluorinated Ethylene Propylene (FEP) coated to avoid any chemical interaction between the micellized liquid nicotine formula and metal canister.

The aerosol pressurized inhalation delivery device eliminates the use of a power source or battery which as used in prior art devices has been known to explode without warning and cause serious injuries including burns, broken bones or even death. The alternative use of a propellant, such as pharma grade Zephex® 152a which is chlorofluorocarbon free and approved by the FDA for use in metered-dose inhalers for the treatment of asthma and other pulmonary obstructive diseases, eliminates the aforementioned safety concerns.

Placing the metal canister into the receptacle housing protects the metal canister from impact and allows the actuator to be positioned on the receptacle housing.

The continuous valve is preferably crimped onto the metal canister with, for example, a metal crimping collette, which couples the continuous valve mounting cup of the continuous valve against the rim of the metal canister. The crimp or an equivalent connector securely holds the metered valve onto the metal canister which once gassed can maintain, by way of example but not limitation, approximately 72 psi (pounds per square inch) pressure inside the metal canister.

The actuator is preferably made from high quality plastic or resinous material, contains an actuator ridged finger control that once depressed activates the continuous valve and delivers the desired volume of micellized liquid nicotine formula to the user. The actuator, once fully depressed downward on the continuous valve, allows the continuous valve's valve stem to be pushed downward into the metal canister releasing micellized liquid nicotine formula under approximately 72 psi through the actuator discharge nozzle.

Depressing and holding down the actuator will allow a controlled amount of liquid micellized formula to be inhaled by the user. Once the user releases the actuator the continuous valve will deactivate the liquid micellized formula from passing through the continuous valve chamber. The continuous valve allows a variable amount of liquid micellized formula to be inhaled to satisfy the user. Some users may determine approximately 100 microliters is an acceptable amount of liquid micellized nicotine formula while others may exceed that volume.

In one aspect, the combination of the micellized liquid nicotine formula and propellant, which in one embodiment may be a propellant known commercially as HFA 134a, becomes miscible, visibly clear, having a viscosity similar to water, creating a homogenous mixture, which makes it easier to deliver a dose of the combined micellized liquid nicotine formula and propellant through the actuator discharge nozzle without having to shake the inhalation delivery device prior to use or prime the $1^{st}$ dose to make sure the dosing chamber fills.

In embodiments, the nicotine formula is preferably micellized, a phase separation of water from oil. This process, referred to herein as micellization, converts an otherwise oil-based product and its ingredients making them bio-absorbable or "bio available" to the body, without changing their molecular form and structure.

Through research and experimentation, the applicant has found that micelles formulated, full spectrum hemp oil ("FSHO") has demonstrated significantly more bioavailability than non-micelles, unformulated hemp-based oils. This means that the FSHO, using micelle technology is more effective, delivering better than 85% absorption to the body, GI tract and/or skin, with a quicker onset than that of traditional, lower dose, FSHO based, or Cannabidiol based products. The same will apply to Tetrahydrocannabinol oil based micellized formulas.

The spirit of this disclosure, in one particular aspect, is to eliminate the use of cartridges or reservoirs or pods, heating elements, power sources or batteries and secondhand smoke in prior art devices, such as vape units, and to replace the corresponding formulas containing nicotine, flavorings, and propylene glycol with a micellized liquid nicotine formula that dramatically decreases the nicotine percentage oral uptake by up to 80%, and helps minimize the known threats of cancer to the user.

E-cigarette's use a battery, the most common called "18650" batteries, which heat up the nicotine vape formula, flavorings and other chemicals and turn them into a vapor the user can inhale. This vapor can contain formaldehyde, heavy metals and other particles that can cause cancer and lodge themselves in the users' deepest parts of the lungs. The present disclosure eliminates the battery or power supply required by e-cigarettes and vaping devices.

In the "News in Health" article presented by the NIH, National Institute of Health, https://newsinhealth.nih.gov/

2020/05/risks-vaping, the risk of vaping is described and acknowledgment is made that "Studies suggest nicotine vaping may be less harmful than traditional cigarettes when people who regularly smoke switch to them as a complete replacement". But nicotine vaping could still damage your health, according to the NIH, because a person must necessarily inhale propylene glycol, vegetable glycerin, and flavorants that were meant to be eaten but not inhaled, not to mention nicotine. When vaping, all of those chemicals are heated up by the power supply and reactor, which may cause those components to turn into other potentially dangerous chemicals.

An object of this disclosure, in another aspect, is to create a reduced harm nicotine aerosol pressurized inhalation delivery device compared to smoking tobacco cigarettes or nicotine vaping using similar components to those employed in pressurized metered dose inhalers, pMDI's, and having a micellized liquid nicotine formula that once inhaled into the lungs delivers greater absorption to the body and significantly lowers the percentage of nicotine inhaled by up to 80% while providing a similar feeling of pleasure for the user.

Various aspects of the present disclosure are shown in FIGS. 1-15. FIG. 1 is a cross-sectional view of aerosol pressurized inhaler delivery device 100 comprising metal canister 132 positioned securely inside protective plastic canister receptacle housing 144 having a continuous valve 102 crimped to metal canister 132 allowing pressurized gas such as, pharma grade Zephex® 152a, 160, and micellized liquid nicotine formula 162 to be introduced into metal canister 132. Depressing actuator ridged finger control 128 allows propellant 160 and micellized liquid nicotine formula 162 to pass through continuous valve 102 and discharge nozzle 120 creating an aerosolized nicotine formula that is inhaled from actuator discharge area 130.

Figure 2:
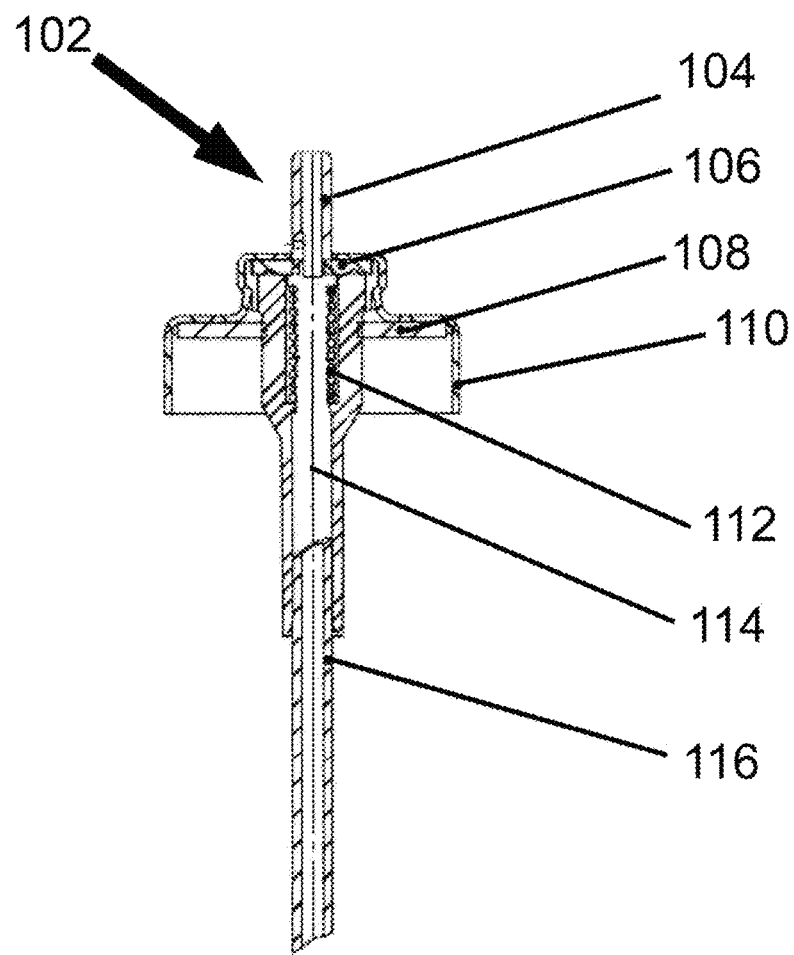
FIG. 2 is a cross sectional view of a continuous valve for the device shown in FIG. 1.

FIG. 2 is a cross-sectional view of continuous valve 102 to be crimped onto metal canister 132 (not shown) via continuous valve mounting cup 110. Once liquid propellant 160 (not shown) is introduced into metal canister 132 (not shown) pressure is created and micellized liquid nicotine formula 162 and liquid propellant 160 (not shown) is released through continuous valve flow chamber 114 drawn up from continuous valve dip tube 116. Once actuator ridged finger control 128 (not shown) is depressed continuous valve stem 104 is pushed downward past continuous valve internal gasket 106 and continuous valve external gasket 108 overcoming resistance from continuous valve spring 112 allowing micellized liquid nicotine formula 162 and liquid propellant 160 (not shown) to be expelled through actuator 118 (not shown). It is known by those skilled in the art that a pressurized liquid substance such as pharma grade Zephex® 152a introduced into metal canister 132 also containing micellized liquid nicotine formula 162 will expand as the outside temperature increases. The pre-determined volume of liquid propellant 160 and pre-determined volume of micellized liquid nicotine formula 162 introduced into the metal canister 132 via a gassing machine is adjusted to allow expansion of the contents when increased outside temperatures are exerted on metal canister 132. The starting pressure of prefilled metal canister 132 is approximately 72 psi, (pounds per square inch), at an outside temperature of approximately 72 degrees Fahrenheit or 22.2 Celsius. Micellized liquid nicotine formula 162, and liquid propellant 160, become homogeneous inside metal canister 132. Air pocket 168 allows safe expansion of liquid propellant 160 and micellized liquid nicotine formula 162 inside metal canister 132 once outside temperatures increase beyond 72 degrees Fahrenheit or 22.2 Celsius.

Figure 3:
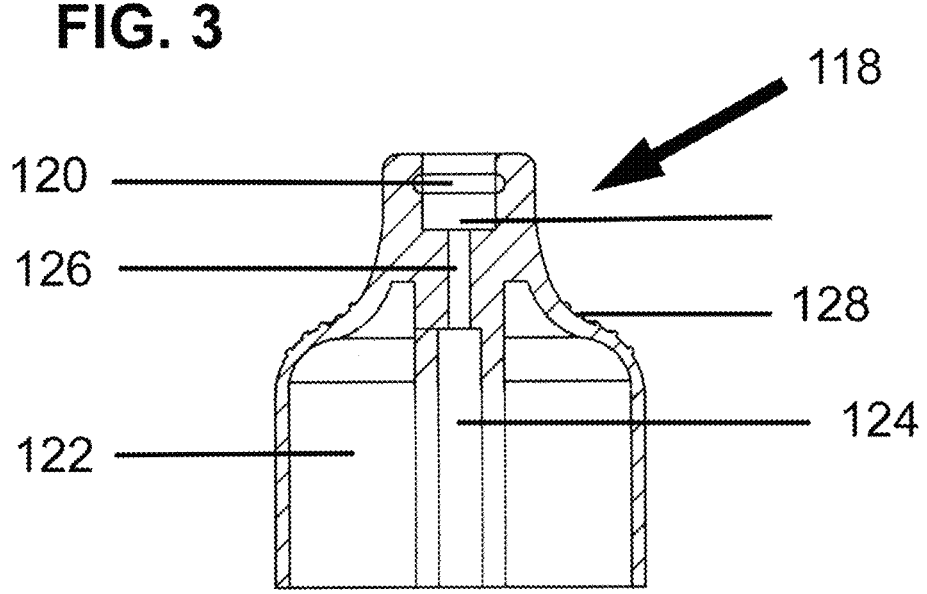
FIG. 3 is a cross-sectional view of an actuator assembly for the device shown in FIG. 1.

FIG. 3 is a cross-sectional view of actuator 118, designed to release a continuous amount of liquid propellant 160 and micellized liquid nicotine formula 162 (not shown) through continuous valve 102 (not shown) positioned on actuator valve sleeve 124. Once actuator ridged finger control 128 is depressed downward, liquid propellant 160 and micellized liquid nicotine formula 162 (not shown) pass through actuator discharge nozzle 120, actuator discharge channel 126, and actuator discharge area 130 allowing liquid propellant 160 and micellized liquid nicotine formula 162 (not shown) to be expelled as an aerosol with particle size of approximately 5 µm to 8 µm (microns) inhaled from actuator discharge area 130.

Figure 4:
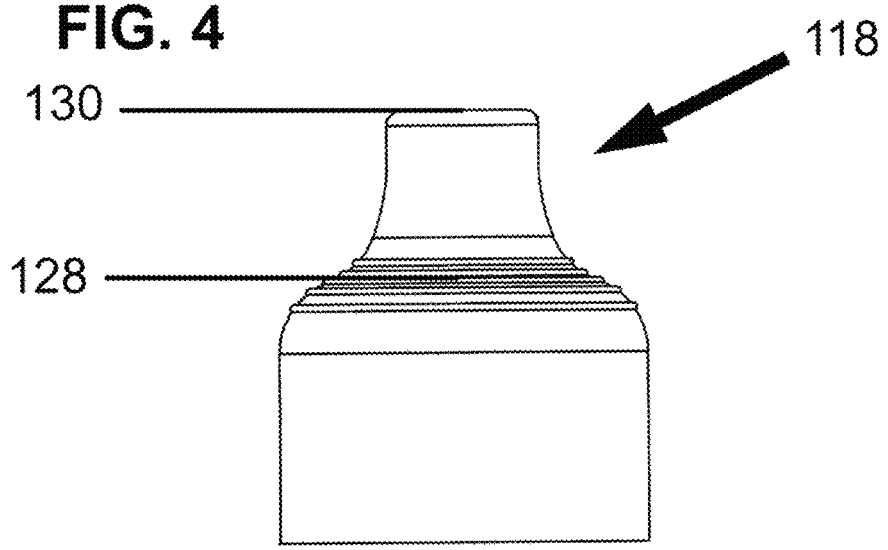
FIG. 4 is a side view of the actuator assembly depicted in FIG. 3.

FIG. 4 is a side view of actuator 118, showing actuator discharge area 130 and actuator ridged finger control 128.

Figure 5:
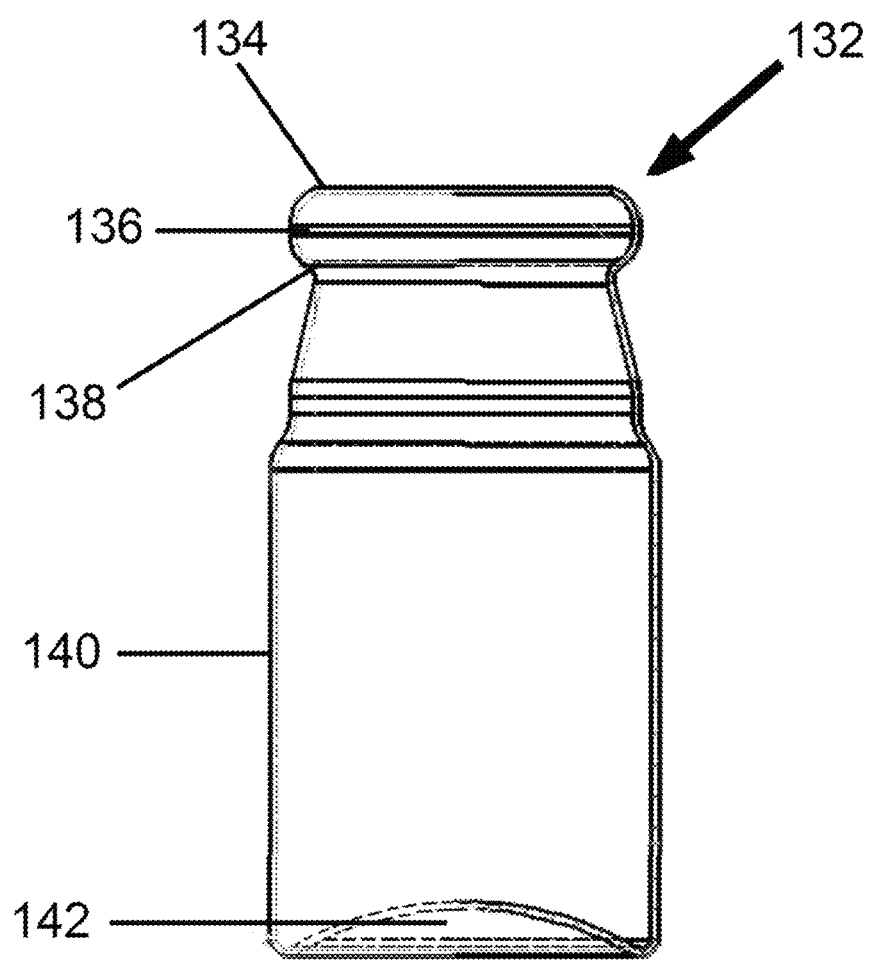
FIG. 5 is a side view of the canister for use with the device shown in FIG. 1.

FIG. 5 shows a side view of metal canister 132 where continuous valve 102 (not shown) resides over metal canister lip 134 and metal canister throat 136 and under metal canister rim 138. When continuous valve 102 (not shown) is crimped to metal canister 132, continuous valve mounting cup 110 (not shown) is held firmly against metal canister rim 138.

Figure 6:
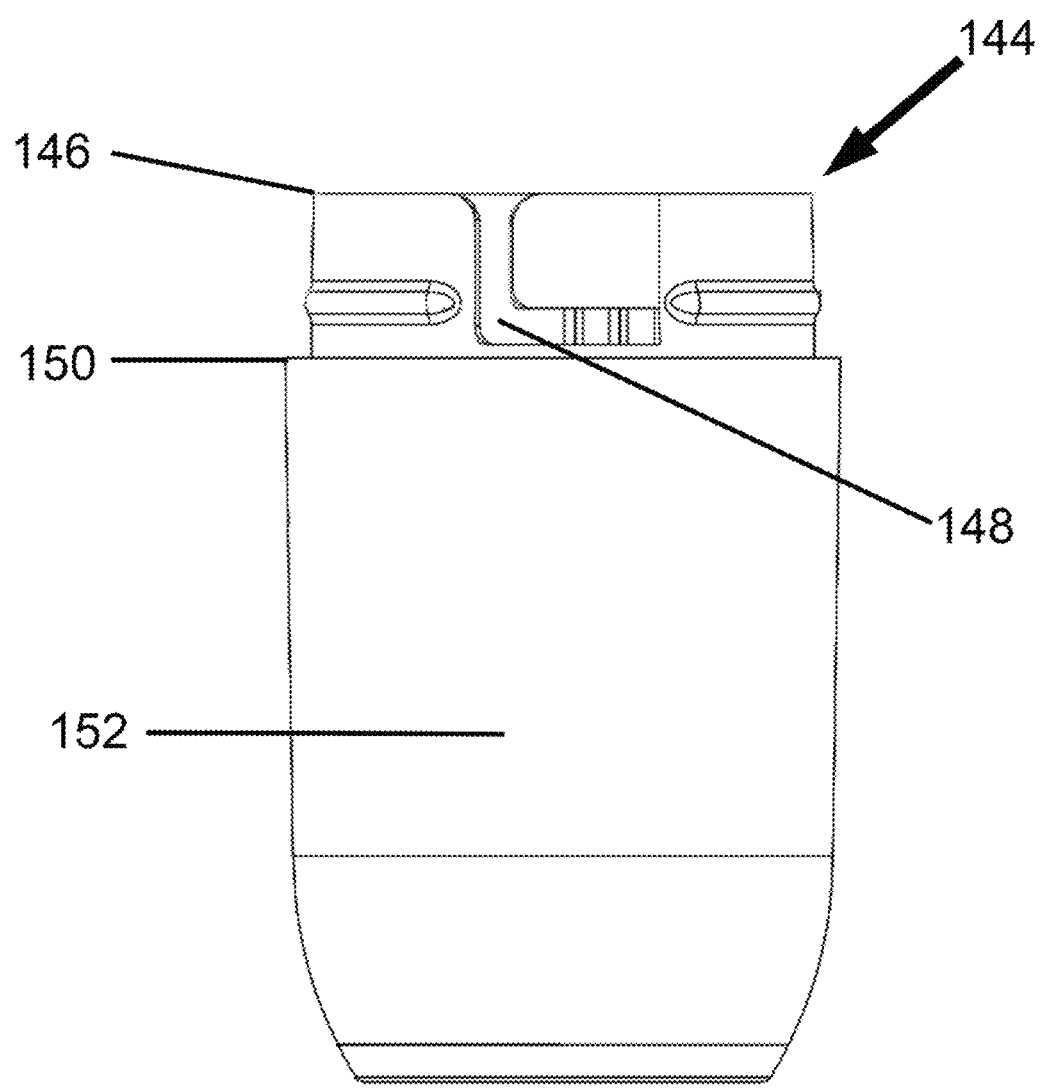
FIG. 6 is a side view of a receptacle housing for the device shown in FIG. 1.

FIG. 6 is a side view of protective plastic canister receptacle housing 144, comprising a protective plastic canister base 152, plastic base receptacle recessed lip 150, plastic base receptacle child resistant cap channels 148 and plastic base receptacle rim 146.

Figure 7:
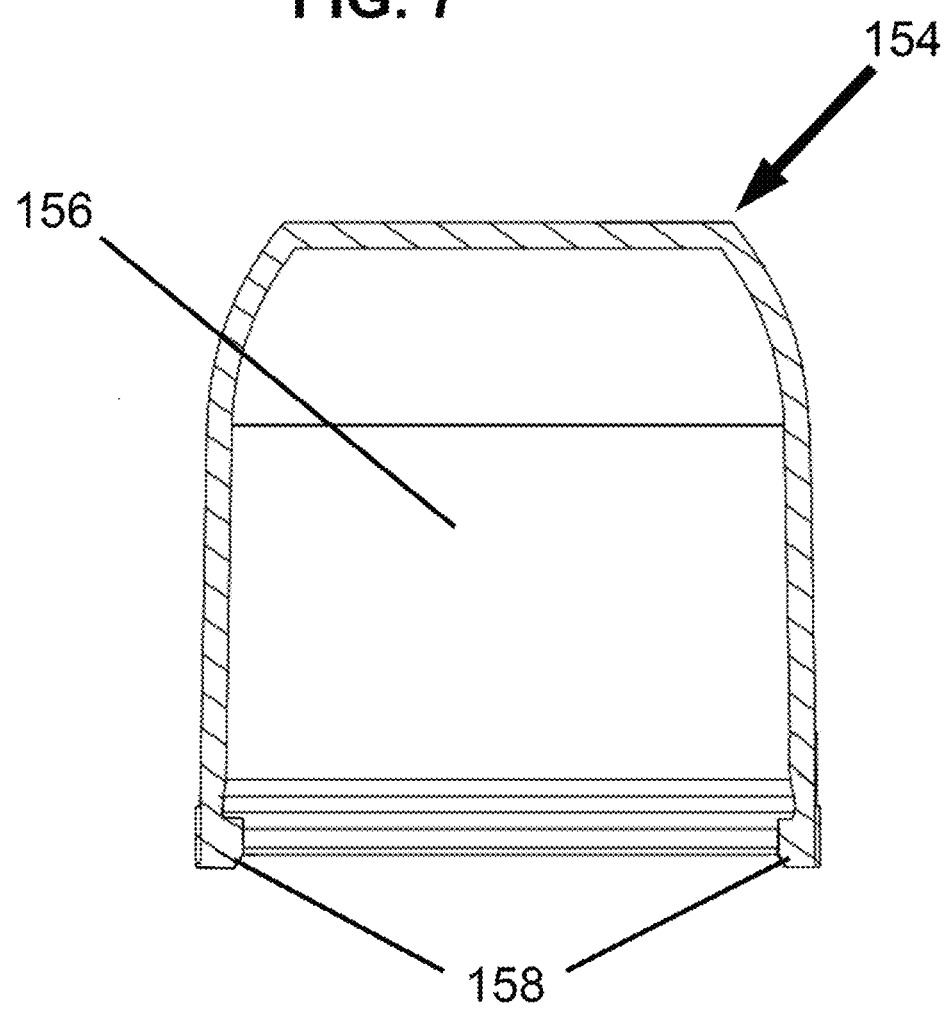
FIG. 7 is a side view of a protective child-resistant cap for use with the device shown in FIG. 1.

FIG. 7 is a side view of protective plastic canister receptacle child resistant cap 154 having protective plastic canister receptacle child resistant cap base 156 and plastic child resistant ribs 158.

Figure 8:
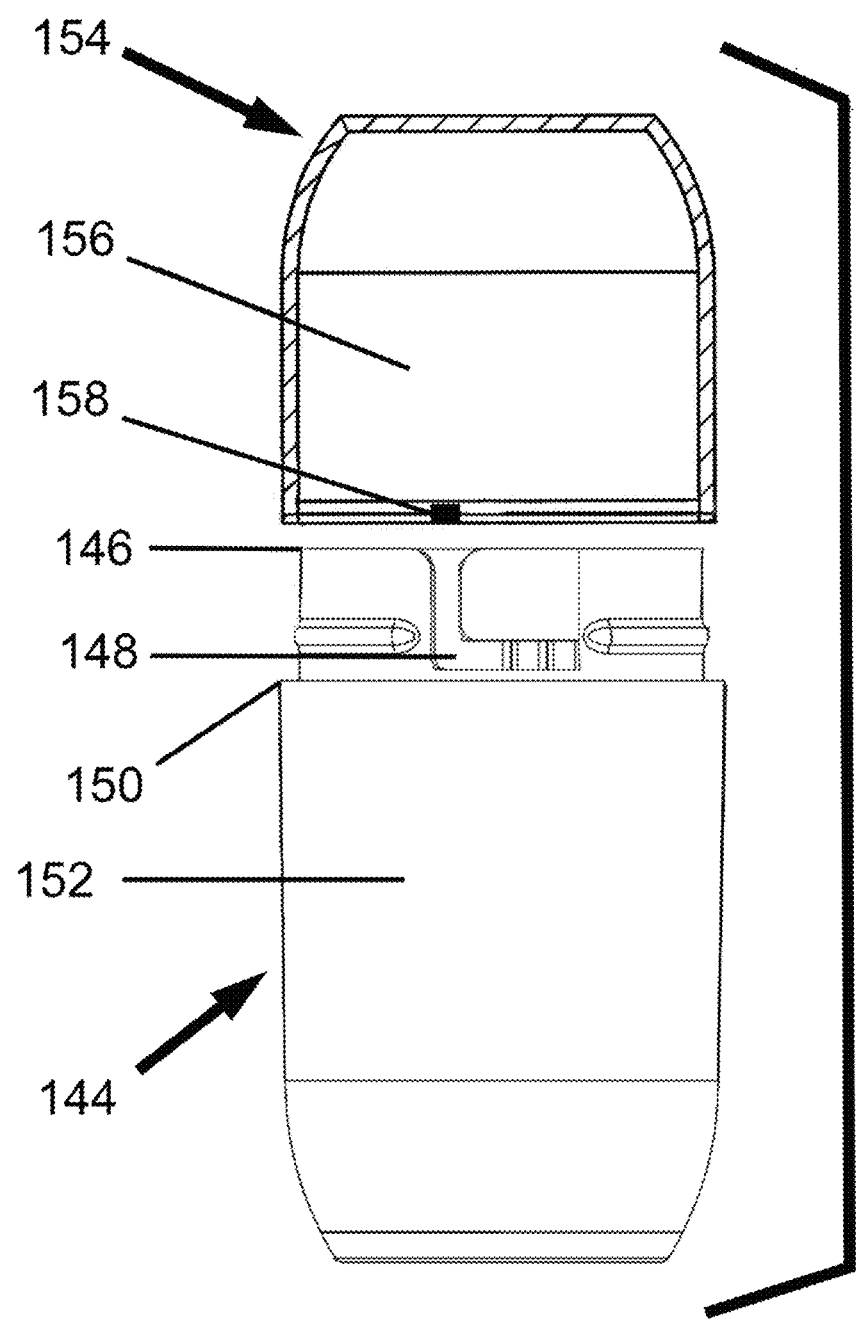
FIG. 8 is a side view of the receptacle housing and protective child-resistant cap shown in FIGS. 6-7.

FIG. 8 is a side view of protective plastic canister receptacle child resistant cap 154 residing over the protective plastic canister receptacle housing 144. Once plastic child resistant ribs 158, located on both sides of protective plastic canister receptacle child resistant cap 154, are aligned above plastic base receptacle child resistant cap channels 148, located on both sides of receptacle housing 144, pushing downward over plastic base receptacle rim 146 and against plastic base receptacle recessed lip 150 and turning counterclockwise through plastic base receptacle child resistant cap channels 148 locks the protective plastic canister receptacle child resistant cap 154 together with protective plastic canister receptacle housing 144.

Figure 9:
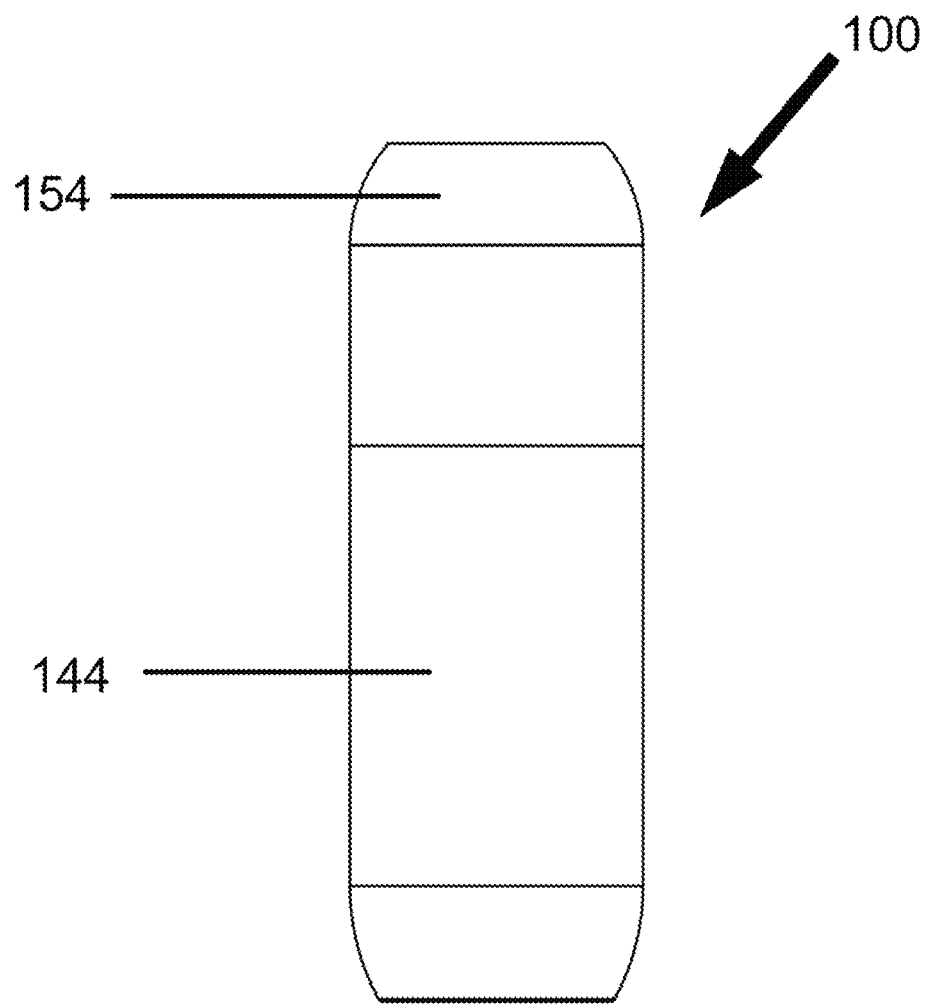
FIG. 9 is a side view of the assembled receptacle housing and protective child-resistant cap.

FIG. 9 is a side view of inhaler aerosol vapor delivery device 100 showing protective plastic canister receptacle child resistant cap 154 attached to protective plastic canister receptacle housing 144. Residing inside inhaler aerosol delivery device 100 are metal canister 132 containing micellized liquid nicotine formula 162, liquid propellant 160 and air pocket 164 with continuous valve 102 crimped onto metal canister 132 and actuator 118 positioned on continuous valve 102 (not shown).

Figure 10:
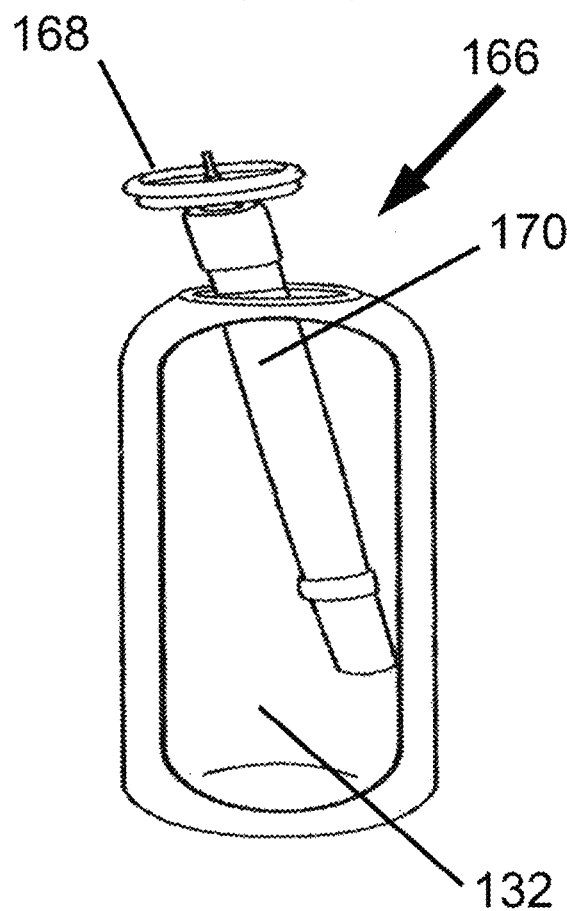
FIG. 10 is a cross-sectional view of an alternate embodiment comprising a bag-on-valve propellant system for use with a metal canister.
Figure 11:
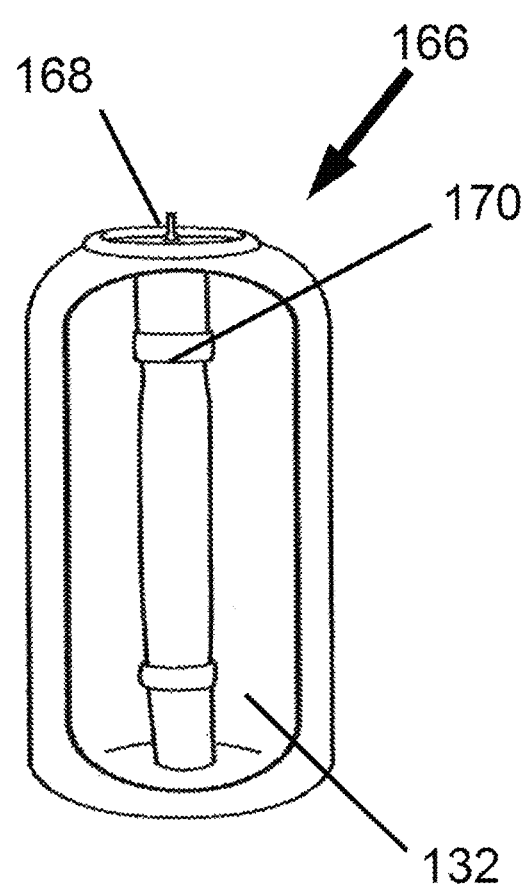
FIGS. 11 is another cross-sectional view of the bag-on-valve system assembled inside of the metal canister of FIG. 10.

FIGS. 10-11 are cross-sectional views of bag-on-valve system 166 depicting insertion of bag-on-valve 170, having bag-on-valve continuous valve 168 attached, into metal canister 132.

Figure 12:
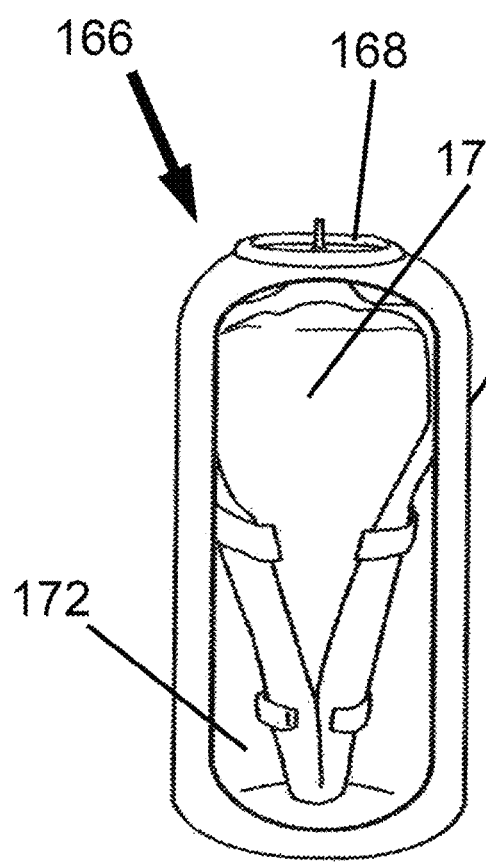
FIG. 12 is a cross-sectional view depicting the bag-on-valve propellant system partially filled with micellized liquid nicotine formula of FIG. 11.
Figure 13:
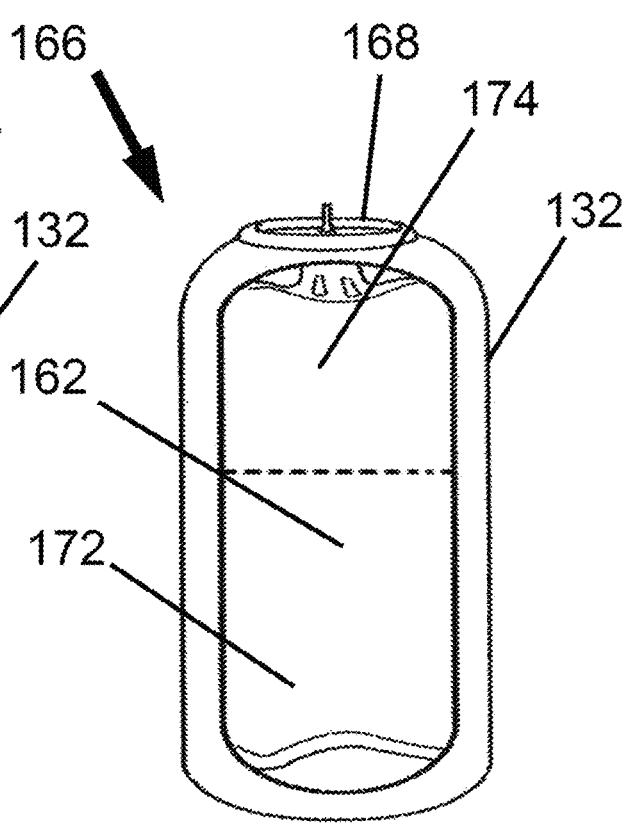
FIG. 13 is another cross-sectional view depicting the bag-on-valve propellant system of FIG. 12, wherein the bag-on-valve bag is substantially filled with micellized liquid nicotine formula.

FIGS. 12-13 are cross-sectional views of a bag-on-valve system 166 depicting the bag-on-valve continuous valve 168 crimped onto metal canister 132, metal canister 132 containing compressed air propellant 172, and bag-on-valve bag 174 containing micellized liquid nicotine formula 162.

FIG. 14 is a side view of the bag-on-valve system 176 with an actuator 118 placed over bag-on-valve continuous valve 168 (not shown) crimped onto a canister 132. Micellized liquid nicotine formula 162 (not shown) resides inside bag-on-valve inflated bag 174.

FIG. 15 is a cross sectional view of the aerosol pressurized inhalation vapor delivery device 176 with insertion of bag-on-valve system 166 into the protective plastic canister receptacle housing 144, further comprising a protective child-resistant cap 154 secured in place.

FIGS. 1-15 may depict more than all of the components required to operate the device. It is also understood that the device design may comprise additional surface features in certain embodiments than those shown in FIGS. 1-15, including surface texturing, coloring, packaging, ergonomic shape, contouring, sheathing, etc. Thus, the embodiments depicted in FIGS. 1-15 are exemplary and non-limiting as to the scope of the present disclosure.

With respect to the embodiments described above, it is expressly understood that such embodiments may be incorporated for use in practicing the novel methods described herein. In certain embodiments, those methods may comprise greater or fewer steps than as described above. By way of example, but not limitation, one step for use with the various embodiments described above may comprise the step of removing and replacing the canister, with different steps included in the method of operation provided accordingly. Thus, variations on this and other steps, and the inclusion or exclusion of additional steps described herein, are expressly contemplated by the present disclosure.

It is expressly understood that where the term "consumer" has been used to describe the various embodiments of the disclosure, the term should not be construed as limiting in any way. For instance, a consumer could be a human user or, in a veterinary application, an animal. Therefore, it is intended that the device and methods described herein apply equally to veterinary science as they would if practiced on a human being. The apparatus and methods described herein therefore have application beyond controlled dosage of nicotine, by way of example.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and/or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. For further illustration, the information and materials supplied with the provisional application from which this application claims priority is expressly made a part of this disclosure and incorporated by reference herein in their entirety. This form of disclosure, therefore, is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A sublingual delivery system, comprising:
    a housing comprising:
        a base portion comprising a recessed lip;
        a cap portion dimensioned to receive the recessed lip of the base portion such that the base portion and cap portion are connected and aligned along a common axis; and
        the base portion and cap portion both comprise an internal void; and
    a pressurized sublingual delivery device comprising:
        a mouthpiece integral with an actuator;
        an actuator discharge nozzle;
        a metered valve;
        a metal canister; and
        a cylindrical receptacle housing:
        wherein the metal canister contains a micellized liquid formula and a propellant;
        wherein the metered valve is crimped to the metal canister;
        wherein the actuator is in contact with and supported by a surface of the metered valve, and is movably coupled to the cylindrical receptacle housing;
        wherein the metal canister is positioned within the cylindrical receptacle housing;
        wherein the mouthpiece, metal canister, metered valve, actuator and cylindrical receptacle housing are all in alignment about the common axis;
        wherein the pressurized sublingual delivery device is positioned within the internal void; and
        wherein the actuator and the metered valve are configured such that, upon axial movement of the actuator with respect to the metered valve, in the direction of the housing cylindrical receptacle, a predetermined dosage of micellized liquid formula is supplied from the metal canister.

2. The sublingual delivery system of claim 1, wherein the predetermined dosage of micellized liquid formula comprises a micellized liquid nicotine formula.

3. The sublingual delivery system of claim 1, wherein the predetermined dosage of micellized liquid formula comprises a micellized liquid cannabidiol formula.

4. The sublingual delivery system of claim 1, wherein the predetermined dosage of micellized liquid formula comprises a micellized liquid tetrahydrocannabinol formula.

5. The sublingual delivery system of claim 1, wherein the predetermined dosage of micellized liquid formula is delivered from the metal canister with each axial movement of the actuator.

6. The sublingual delivery system of claim 1, wherein the predetermined dosage of micellized liquid formula is in the range of 50 to 100 microliters.

7. The sublingual delivery system of claim 1, wherein the predetermined dosage of micellized liquid formula is 100 microliters.

8. The sublingual delivery system of claim 1, wherein the predetermined dosage of micellized liquid formula is 65 microliters.

9. The sublingual delivery system of claim 1, wherein the predetermined dosage of micellized liquid formula comprises at least a nicotine salt.

10. The sublingual delivery system of claim 1, wherein the predetermined dosage of micellized liquid formula is delivered through the actuator discharge nozzle.

11. The sublingual delivery system of claim 1 further comprising a bag-on-valve bag coupled to the metal canister.

* * * * *